(12) United States Patent
Madon et al.

(10) Patent No.: US 10,537,886 B2
(45) Date of Patent: Jan. 21, 2020

(54) SPRAY-DRIED BUTYNEDIOL CATALYSTS

(71) Applicant: BASF CORPORATION, Florham Park, NJ (US)

(72) Inventors: Rostam Jal Madon, Flemington, NJ (US); Peter Nagel, Highlands, NJ (US); Keenan Lee Deutsch, Highland Park, NJ (US); Deepak S. Thakur, Solon, OH (US)

(73) Assignee: BASF CORPORATION, Florham Park, NJ (US)

( * ) Notice: Subject to any disclaimer, the term of this patent is extended or adjusted under 35 U.S.C. 154(b) by 0 days.

(21) Appl. No.: 15/754,261

(22) PCT Filed: Aug. 23, 2016

(86) PCT No.: PCT/US2016/048183
§ 371 (c)(1),
(2) Date: Feb. 21, 2018

(87) PCT Pub. No.: WO2017/035133
PCT Pub. Date: Mar. 2, 2017

(65) Prior Publication Data
US 2018/0236439 A1 Aug. 23, 2018

Related U.S. Application Data

(60) Provisional application No. 62/209,485, filed on Aug. 25, 2015.

(51) Int. Cl.

| | | |
|---|---|---|
| *B01J 23/72* | (2006.01) | |
| *B01J 37/12* | (2006.01) | |
| *B01J 38/00* | (2006.01) | |
| *B01J 37/00* | (2006.01) | |
| *C07C 29/42* | (2006.01) | |
| *B01J 23/843* | (2006.01) | |
| *B01J 35/02* | (2006.01) | |
| *B01J 21/04* | (2006.01) | |
| *B01J 21/08* | (2006.01) | |
| *B01J 21/16* | (2006.01) | |
| *B01J 21/18* | (2006.01) | |
| *B01J 27/232* | (2006.01) | |
| *B01J 37/08* | (2006.01) | |
| *C07C 33/046* | (2006.01) | |

(52) U.S. Cl.
CPC .......... *B01J 37/0045* (2013.01); *B01J 21/04* (2013.01); *B01J 21/08* (2013.01); *B01J 21/16* (2013.01); *B01J 21/18* (2013.01); *B01J 23/8437* (2013.01); *B01J 27/232* (2013.01); *B01J 35/023* (2013.01); *B01J 37/08* (2013.01); *C07C 29/42* (2013.01); *C07C 33/046* (2013.01)

(58) Field of Classification Search
CPC ... B01J 21/04; B01J 21/08; B01J 21/16; B01J 21/18; B01J 23/72; B01J 23/8437; B01J 35/023; B01J 37/08; B01J 37/12; B01J 38/00; C07C 29/42; C07C 33/046
USPC ................................ 502/184, 244, 246, 345
See application file for complete search history.

(56) References Cited

U.S. PATENT DOCUMENTS

| | | | | |
|---|---|---|---|---|
| 2,768,215 A | * | 10/1956 | Hecht | ............... C07C 29/42 502/244 |
| 3,294,849 A | * | 12/1966 | Hecht | ............ B01J 23/8437 502/152 |
| 3,560,576 A | | 2/1971 | Kirchner | |
| 3,650,985 A | | 3/1972 | Kirchner | |
| 3,920,759 A | | 11/1975 | Hort | |
| 4,002,694 A | | 1/1977 | Hort | |
| 4,107,082 A | | 8/1978 | Fremont | |
| 4,119,790 A | | 10/1978 | Hort | |
| 4,584,418 A | * | 4/1986 | Fremont | ............. B01J 27/232 502/174 |
| 7,348,383 B2 | | 3/2008 | Zoeckler et al. | |
| 2014/0275639 A1 | | 9/2014 | Madon et al. | |

FOREIGN PATENT DOCUMENTS

| | | | | | |
|---|---|---|---|---|---|
| CN | 10 2658158 | * | 9/2012 | ............ | B01J 23/843 |
| CN | 102658158 A | | 9/2012 | | |
| CN | 10 2950002 | * | 3/2013 | ............ | B01J 23/843 |
| CN | 10 3480382 | * | 1/2014 | ............ | B01J 23/843 |
| CN | 10 3638937 | * | 3/2014 | ............ | B01J 23/843 |
| CN | 102950002 B | | 6/2014 | | |
| GB | 1 501 155 A | | 2/1978 | | |
| WO | WO-2010/119448 A1 | | 10/2010 | | |

OTHER PUBLICATIONS

Guihua Yang et al., "MCM-41 supported CuO/Bi2O3 nanoparticles as potential catalyst for 1,4-butynediol synthesis." Ceramics International 40, pp. 3969-3973. (Year: 2014).*
International Search Report & Written Opinion in International Application No. PCT/US2016/048183, dated Nov. 18, 2016 (11 pages).
Chu et al., "Kinetics of the synthesis of 1,4-butynediol over a copper-bismuth/magnesium silicate catalyst," Applied Catalysis A: General, vol. 7, Issue 2, (Apr. 1993) 123-132. (Abstract only).
Extended European Search Report in EP application No. 16839985. 5, dated Mar. 19, 2019 (8 pages).

* cited by examiner

*Primary Examiner* — Patricia L. Hailey
(74) *Attorney, Agent, or Firm* — Foley & Lardner LLP

(57) ABSTRACT

A process of forming an ethynylation catalyst includes providing a slurry including water, a copper-containing material, a bismuth-containing material, a structural material, and a binder; spray-drying the slurry to form particles; and calcining the particles to form the ethynylation catalyst.

15 Claims, No Drawings

SPRAY-DRIED BUTYNEDIOL CATALYSTS

CROSS-REFERENCE TO RELATED APPLICATIONS

This application is a U.S. National Phase Application under 35 U.S.C. § 371 of International Application No. PCT/US2016/048183, filed on Aug. 23, 2016, which claims priority to U.S. Provisional Application No. 62/209,485, filed Aug. 25, 2015, the contents of which are incorporated herein by reference in their entireties.

FIELD

The present technology is generally related to catalysts for the production of butynediol. More specifically, the technology is related to methods of preparing such catalysts.

BACKGROUND

The catalytic ethynylation of formaldehyde is known as the "Reppe Reaction," or "Reppe Process." Known processes of forming copper-containing catalysts used in the Reppe process include impregnation of silicate supports, co-precipitation, and deposition precipitation. However, uniform material preparation remains a challenge.

SUMMARY

In one aspect, a process of forming an ethynylation catalyst is provided. The process includes providing an aqueous slurry comprising water, a copper-containing material, a bismuth-containing material, a structural material, and a binder; spray-drying the slurry to form particles; and calcining the particles to form the ethynylation catalyst. Illustrative copper-containing materials may include, but are not limited to, copper carbonate, copper oxalate, copper hydroxide, cupric oxide, and cuprous oxide. Illustrative bismuth-containing materials may include, but are not limited to, bismuth carbonate, bismuth oxalate, bismuth hydroxide, bismuth oxide, and bismuth acetate. Illustrative structural materials may include, but are not limited to, a clay, talc, calcium silicate, kieselguhr, alumina, carbon, and silica. Illustrative binders may include, but are not limited to, a silica sol, an alumina sol, sodium silicate, and aluminum chlorohydrate.

In any of the above embodiments, the particles may have an average particle diameter of about 5 µm to about 100 µm.

In another aspect, the ethynylation catalyst formed according to any of the above embodiments is provided.

In another aspect, a process of activating an ethynylation catalyst is provided. The process includes providing the ethynylation catalyst made by any of the above processes; exposing the ethynylation catalyst to formaldehyde to form a mixture; and maintaining the mixture at a sufficient temperature for a sufficient time to form an activated ethynylation catalyst. In some embodiments, the sufficient temperature is about 80° C. In some embodiments, the sufficient time is from about 1 hour to about 10 hours. In any of the above embodiments, the activated ethynylation catalyst includes a copper acetylide species.

In another aspect, the activated ethynylation catalyst formed according to the above processes is provided.

In another aspect, a process of forming 1,4-butynediol is provided. This process includes, the exposing the activated ethynylation catalyst described above to acetylene in the presence of formaldehyde at a sufficient temperature for a sufficient time to produce 1,4-butynediol.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Generally, a process of preparing a particulate catalyst via spray-drying is provided. After spray-drying the catalyst particles are calcined in air. The particulate catalyst contains copper oxide, bismuth oxide, a structural material, and a binder. The particulate catalyst is useful for the ethynylation of formaldehyde to form 1,4-butynediol, i.e. it is an ethynylation catalyst.

In one aspect, a process is provided for preparing a particulate catalyst via spray-drying. The process uses a metal-containing precursor of the copper or bismuth oxides of the particulate catalyst. For example, metal-containing precursors may include carbonates, oxalates, citrates, sulfates, nitrates, and hydroxides. The precursor salt(s) are suspended, not dissolved, in a solvent such that a slurry is formed. The slurry may be milled until a desired particle size in the slurry is achieved. Alternatively, the precursor salts may be dry milled either individually, or together until a desired particle size is achieved, prior to formation of the slurry.

The average particle size (APS) may be from less than about 0.5 µm to about 10 µm. In some embodiments, the APS may be from about 0.5 µm to about 5 µm. In some embodiments, the APS may be from about 0.5 µm to about 3 µm. In some embodiments, the APS may be from about 1 µm to about 2 µm. In some embodiments, the APS is less than about 2 µm. Milling of the precursors may be continued for as long, or as short, as needed to achieve a desired particle size and particle size distribution. This may be from about 15 minutes to about 24, in some embodiments. In other embodiments, the time of milling may be from about 2 hours to about 20 hours. In some embodiments, the time of milling is from about 10 hours to about 20 hours.

Illustrative materials for structural material precursor, include, but are not limited to, clay, talc, calcium silicate, kieselguhr, alumina, carbon, and silica. The structural component aids in the overall functionality of the catalyst. As with the precursor salts above, the structural component may be milled to provide a slurry of the material, or a material of appropriate particle size may be obtained and suspended to provide a slurry, or a pre-prepared slurry may be obtained.

The milling and slurrying of the precursor salts and structural materials may be carried out in any appropriate solvent. For example, the solvent may be water, an alcohol, a nitrile, a ketone, or an ether. In some embodiments, water is the solvent. Accordingly, in some embodiments, the slurry formed is an aqueous slurry.

Upon formation of a slurry of the precursor salt and structural material, a binder may be added to the slurry. Illustrative binders may include, but are not limited to silica sols, alumina sols, sodium silicate, and aluminum chlorohydrate. In some embodiments, the binder is $SiO_2$. The amount of binder in the slurry is an amount necessary to bind the final catalyst. The amount may be from about 1 wt % to about 30 wt % based upon total solids. In some embodiments, the amount is from about 5 wt % to about 20 wt %. In other embodiments, the amount is about 10 wt % binder based upon total solids.

At this stage of the process, the slurry is adjusted in solids content such that when spray-drying is conducted the materials are readily flowable and sprayed. For example, the solids content of the slurry may be adjusted to a value of about 1 wt % to about 50 wt %. In some embodiments, the solids content of the slurry may be adjusted to a value of about 1 wt % to about 25 wt %. In some embodiments, the solids content of the slurry may be adjusted to a value of about 2 wt % to about 20 wt %. In some embodiments, the solids content of the slurry may be adjusted to a value of about 5 wt % to about 15 wt %. In some embodiments, the solids content of the slurry may be adjusted to about 10 wt %. Additional solvent may be added, or solvent may be removed, to achieve the desired solids content of the slurry.

The process of the spray-drying the slurry of the precursor salts, structural material, and binder may be carried out with a standard wheel spray-dryer, or a nozzle-type spray-dryer. The resulting powder has an average particle diameter of about 5 μm to about 100 μm. In some embodiments, the average particle diameter is about 5 μm to about 60 μm. In some embodiments, the average particle diameter is about 10 μm to about 20 μm. In some embodiments, the average particle diameter is about 15 μm to about 40 μm. In some embodiments, the average particle diameter is about 15 μm. After obtaining the powder it is calcined at a temperature from about 250° C. to 600° C. to form a powdered, calcined catalyst material. In some embodiments, the calcination temperature is from 350° C. to 500° C.

After calcination the powdered, calcined catalyst material contains about 20 wt % to about 70 wt % copper oxide, and about 1 wt % to about 5 wt % bismuth oxide. Sodium levels (as $Na_2O$) are typically less than about 3 wt %. The balance of the powdered, calcined catalyst material is mostly a variety of oxides that depend on the specific structural material used. For example, talc contains the both Mg and Si, clay contains Al and Si, calcium silicate contains Ca and Si, and binder may contain Si. Impurities in small amounts may be present.

After catalyst formation, it may be activated for ethynylation reactions. The powdered, calcined catalyst is mixed with formaldehyde in water, and the pH is adjusted to a slightly basic value. For example, the pH may be adjusted to a value from greater than about 7 to about 10. In some embodiments, the pH is adjusted to about 8. The adjust of the pH is necessary to prevent or mitigate formic acid formation which would otherwise react with the copper-containing materials, thereby dissolving the copper into solution, rather than maintaining it as a slurry. The reaction of the catalyst with the formaldehyde produces an active Cu(I) acetylide species ($Cu_2C_2$).

The activated catalyst is then exposed to acetylene in a pressurized reactor in the presence of addition formaldehyde in water. The reaction with acetylene is carried out in an inert atmosphere where the acetylene is co-mixed with a gas such as nitrogen, argon, or helium. The reactor is gradually heated from room temperature to about 80° C. After a period of time for reaction, evidenced by reduced acetylene uptake of the catalyst, the reactor is cooled under an acetylene flow. The reactor is purged with nitrogen and the product containing 1,4-butynediol and propargyl alcohol is recovered.

The above procedures provide a simplified method of the described catalysts. The catalysts produced show activity that is comparable to, or superior to, the commercial catalysts for formation of 1,4-butynediol.

The present invention, thus generally described, will be understood more readily by reference to the following examples, which are provided by way of illustration and are not intended to be limiting of the present invention.

EXAMPLES

Example 1

Copper carbonate and bismuth carbonate are mixed with water to about 30 wt % solids level and slurried. The slurry is then added to a batch-type ball mill (60% balls volume) and rotated on a roller stand for 16 hours, or until the average particle size (APS), or $d_{50}$, is about 1 to 2 micrometers (μm). Talc or other structural components may, if necessary, also undergo the same type of milling procedure, unless it is commercially available in the 2 or lower micron APS. The milled slurry (water, copper carbonate, bismuth carbonate, structural material) is then combined with the binder, $SiO_2$ (commercially available as Ludox® AS40 or Ludox® HS40), such that the overall binder level is about 10 wt %. Additional water may be added so that a predetermined overall solids content is obtained—about 10 wt % solids. The resulting slurry with about 10 wt % solids is then pumped to a spray-dryer, spray-dried, and the product is collected as a powder. The powder is then calcined at a temperature from about 250° C. to about 600° C., more normally at 350° C. to 500° C.

The spray drier conditions are as set forth in Table 1, below.

TABLE 1

General Spray-Drier Conditions.

| Variable | Setting |
|---|---|
| Inlet Temperature (° C.) | 325 |
| Outlet Temperature (° C.) | 110 |
| Wheel Speed (calculated, rpm) | 30,000 |
| Particle Size Target ($d_{50}$, μm) | 10-25 |

After calcination the catalyst contains about 20 wt % to about 60 wt % copper oxide, and about 1.0 wt % to about 4.5 wt % bismuth oxide. Sodium levels (as $Na_2O$) are typically less than about 3 wt %. The balance of the catalyst is mostly a variety of oxides that depend on the specific structural material used. For example, talc contains the both Mg and Si, clay contains Al and Si, calcium silicate contains Ca and Si, and Ludox® contains the Si. Impurities in small amounts may be present. Various samples and their components for spray-drying, including weights, are provided in Table 2, and Table 3 provides data and conditions of formation for the components used in the various samples.

TABLE 2

Slurry Components For Spray-Drying

| Component | Solids (g) | Water (g) | Total Solids and Water (g) | Slurry Solids (%) |
|---|---|---|---|---|
| Sample 1 | | | | |
| $CuCO_3$ + $Bi_2(CO_3)_3$ (milled) | 164.4 | 431.2 | 595.6 | 27.60 |
| M93 calcined clay (milled) | 89.6 | 89.6 | 179.2 | 50.00 |
| $SiO_2$ Binder (Ludox® AS40) | 20.0 | 30.0 | 50.0 | 40.00 |
| Total | 274.0 | 550.8 | 824.8 | |
| Water (for 10.9 wt % total solids) | | | 1960.0 | |
| Sample 2 | | | | |
| $CuCO_3$ + $Bi_2(CO_3)_3$ (milled) | 164.4 | 431.2 | 595.6 | 27.60 |
| Calcium Silicate (milled) | 89.6 | 209.1 | 298.7 | 30.0 |
| $SiO_2$ Binder (Ludox® AS40) | 20.0 | 30.0 | 50.0 | 40.00 |
| Total | 274.0 | 670.3 | 944.3 | |
| Water (for 10 wt % total solids) | | | 1800.0 | |
| Sample 3 | | | | |
| $CuCO_3$ + $Bi_2(CO_3)_3$ (milled) | 164.4 | 424.8 | 589.2 | 27.9 |
| Talc (Mg/Si; reagent grade; milled) | 89.6 | 220.1 | 309.1 | 28.9 |
| $SiO_2$ Binder (Ludox® AS40) | 20.0 | 30.0 | 50.0 | 40.00 |
| Total | 274.0 | 674.9 | 948.9 | |
| Water (for 10 wt % total solids) | | | 1800.0 | |
| Sample 4 | | | | |
| $CuCO_3$ + $Bi_2(CO_3)_3$ (milled) | 164.4 | 402.4 | 566.8 | 29 |
| Talc (Mg/Si; Cimtuff 9102; not milled) | 89.6 | 226.0 | 315.6 | 28.4 |
| $SiO_2$ Binder (Ludox® AS40) | 20.0 | 30.0 | 50.0 | 40.00 |
| Total | 274.0 | 674.9 | 948.9 | |
| Water (for 9.8 wt % total solids) | | | 1850.0 | |
| Sample 5 | | | | |
| $CuCO_3$ + $Bi_2(CO_3)_3$ (milled) | 164.4 | 402.4 | 566.8 | 29 |
| Talc (Mg/Si; Cimtuff 9102; milled) | 89.6 | 226.0 | 315.6 | 28.4 |
| $SiO_2$ Binder (Ludox® HS40) | 20.0 | 30.0 | 50.0 | 40.00 |
| Total | 274.0 | 674.9 | 948.9 | |
| Water (for 9.8 wt % total solids) | | | 1850.0 | |
| Sample 6 | | | | |
| $CuCO_3$ + $Bi_2(CO_3)_3$ (milled) | 164.4 | 402.4 | 566.8 | 29 |
| Talc (Mg/Si; Cimtuff 9102; milled) | 89.6 | 226.0 | 315.6 | 28.4 |
| $SiO_2$ Binder (Ludox® HS40) | 20.0 | 30.0 | 50.0 | 40.00 |
| Total | 274.0 | 674.9 | 948.9 | |
| Water (for 9.8 wt % total solids) | | | 1850.0 | |

TABLE 3

Catalyst Component and Preparation Condition Data

| | Sample | | | | | |
|---|---|---|---|---|---|---|
| | 1 | 2 | 3 | 4 | 5 | 6 |
| Calcination Temp. (° C.) | 400 | 400 | 400 | 400 | 400 | 500 |
| CuO (wt %) | 40.88 | 61.01 | 40.23 | 39.36 | 43.80 | 43.80 |
| $SiO_2$ (wt %) | 34.62 | 25.04 | 37.47 | 38.46 | 37.95 | 37.95 |
| MgO (wt %) | — | 2.72 | 18.30 | 19.00 | 16.40 | 16.40 |
| $Bi_2O_3$ (wt %) | 2.17 | 3.43 | 2.19 | 2.06 | 1.67 | 1.67 |
| CaO (wt %) | — | 6.55 | — | — | — | — |
| $Al_2O_3$ (wt %) | 22.33 | 1.24 | 1.81 | 1.12 | 1.18 | 1.18 |
| Particle Size APS (μm) | 8.7 | 15.4 | 21.5 | 17.9 | 18.5 | 18.5 |

Example 2

Catalyst Testing Procedure. Testing was generally carried out in two steps. First, the catalyst was activated to form an active copper acetylide. Second, the active copper acetylide was then transferred to the reaction vessel.

Specifically, catalyst activation was carried out in a 4-port quartz reactor flask containing 100 mL formalin (37 wt % formaldehyde in water). The pH of the formalin was adjusted to about 8 by adding 1.5 M NaOH. The neat formalin is acidic (pH=3 to 4) due to formic acid impurities. This acid must be neutralized prior to contacting the catalyst with formalin or the copper in the catalyst may form copper formates and dissolve in solution. Next, 15 g of powdered, calcined catalyst were added to the pH adjusted formalin. The reactor was purged with nitrogen, stirring was started, and acetylene was introduced at 50 mL/min to the catalys-formalin slurry at room temperature. The flask was then lowered into a recirculating water bath and heated to 80° C. This procedure forms the active Cu(I) acetylide species $[Cu_2C_2]$.

The formic acid produced was continuously neutralized by adding 1.5 M NaOH to the slurry, thereby maintaining the pH at about 8. After 5 hours, the reactor was cooled to room temperature under flowing acetylene. Once at reached room temperature, the acetylene was purged from the flask with nitrogen, the reactor was disassembled, and the slurry removed. It was weighed, centrifuged, and decanted, leaving wet catalyst ready for activity testing.

Example 3

Reaction Testing. Reaction studies were carried out using 0.5 g of the activated catalyst (dry basis) loaded into a stainless steel stirred autoclave containing 45 mL formalin. As with the activation procedure, the pH of the formalin was initially adjusted to about 8. The reactor was purged with nitrogen and acetylene before starting the reaction. The reactor was operated in a semi-batch fashion while stirring at 1450 RPM. At the start, acetylene from pressurized ballast cylinders was introduced to the reactor through a pressure regulator set at 15 psig (the reaction pressure), and the reactor was heated at approximately 2° C. per min to 80° C. NOTE: the reactor should not be heated in the absence of acetylene or the Cu acetylides will reduce to $Cu^0$, deactivating the catalyst. As the reaction progressed, acetylene uptake was monitored via pressure changes in the ballast cylinders. After 5 hours, the reactor was cooled in flowing acetylene and subsequently purged with nitrogen. The slurry was removed, centrifuged, and decanted. The product mixture was analyzed by gas chromatography. 1,4-butynediol (primary product) and propargyl alcohol (product intermediate) were quantified.

Example 4

Activity Comparison. The activity of the catalysts measured as described above is provided in Table 4. The activities are compared to the commercial BASF catalyst Cu 5020P, as a control. The activity is reported as mols of butynediol plus propargyl alcohol formed per min per g of CuO. Note that the powder, calcined catalysts made via the above spray-drying methods are similar to, or superior to, the commercial catalyst.

TABLE 4

Activity Comparison Data

| Sample | Rate of butynediol and propargyl alcohol formed (mol/min/g CuO) |
|---|---|
| Control | $2.73 \times 10^{-4}$ |
| 1 | $2.63 \times 10^{-4}$ |
| 2 | $2.83 \times 10^{-4}$ |
| 3 | $2.88 \times 10^{-4}$ |
| 4 | $2.91 \times 10^{-4}$ |
| 5 | $2.81 \times 10^{-4}$ |
| 6 | $3.14 \times 10^{-4}$ |

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A process of forming an ethynylation catalyst, the process comprising:
   providing an aqueous slurry comprising water, a copper-containing material, a bismuth-containing material, a structural material, and a binder;
   spray-drying the slurry to form particles; and
   calcining the particles to form the ethynylation catalyst.

2. The process of claim 1, wherein the copper-containing material comprises copper carbonate, copper oxalate, copper hydroxide, cupric oxide, or cuprous oxide.

3. The process of claim 1, wherein the bismuth-containing material comprises bismuth carbonate, bismuth oxalate, bismuth hydroxide, bismuth oxide, and bismuth acetate.

4. The process of claim 1, wherein the structural material comprises a clay, talc, calcium silicate, kieselguhr, alumina, carbon, or silica.

5. The process of claim 1, wherein the binder comprises a silica sol, an alumina sol, sodium silicate, or aluminum chlorohydrate.

6. The process of claim 1, wherein the particles have an average particle diameter of about 5 μm to about 100 μm.

7. The process of claim 1, wherein the particles have an average particle diameter of about 5 μm to about 60 μm.

8. The process of claim 1, wherein the particles have an average particle diameter of about 15 μm.

9. The ethynylation catalyst formed according to claim 1.

10. A process of activating an ethynylation catalyst, the process comprising:
   providing the ethynylation catalyst of claim 9;
   exposing the ethynylation catalyst to formaldehyde to form a mixture; and maintaining the mixture at a sufficient temperature for a sufficient time to form an activated ethynylation catalyst.

11. The process of claim 10, wherein the sufficient temperature is about 80° C.

12. The process of claim 10, wherein the sufficient time is from about 1 hour to about 10 hours.

13. The process of claim 10, wherein the activated ethynylation catalyst comprises a copper acetylide species.

14. The activated ethynylation catalyst formed according to the process of claim 10.

15. A process of forming 1,4-butynediol, the process comprising:
    exposing the activated ethynylation catalyst of claim 14 to acetylene in the presence of formaldehyde at a sufficient temperature for a sufficient time to produce 1,4-butynediol.

\* \* \* \* \*